United States Patent [19]
Farella et al.

[11] 4,200,804
[45] Apr. 29, 1980

[54] SYSTEM FOR TRANSPORTING, STORING AND INJECTING RADIOISOTOPE-CONTAINING FLUIDS

[75] Inventors: Ralph Farella, Scarsdale, N.Y.; Barry Dansky, Fairfield, Conn.; Leonard Epifano, Rye, N.Y.

[73] Assignee: Medi-Ray, Inc., Tuckahoe, N.Y.

[21] Appl. No.: 914,171

[22] Filed: Jun. 9, 1978

Related U.S. Application Data

[63] Continuation of Ser. No. 747,557, Dec. 6, 1976, abandoned.

[51] Int. Cl.$^2$ .................. G21F 5/00; G01N 21/24
[52] U.S. Cl. .................. 250/506; 250/432 R; 250/515
[58] Field of Search .................. 250/506, 432, 515

[56] References Cited
U.S. PATENT DOCUMENTS

| | | | |
|---|---|---|---|
| 3,673,411 | 6/1972 | Glasser | 250/506 |
| 3,973,554 | 8/1976 | Tipton | 250/506 |
| 4,056,096 | 11/1977 | Collica et al. | 250/506 |
| 4,060,073 | 11/1977 | Collica et al. | 250/506 |

*Primary Examiner*—Harold A. Dixon
*Attorney, Agent, or Firm*—Martin Novack

[57] ABSTRACT

The invention is a system for transporting, storing, and injecting of radioactive isotopes, the system including a unit dose of radioactive isotope-containing fluid loaded in a disposable shielded syringe. There is provided a syringe body including a barrel and a plunger slideable in the barrel and extending from the rear of the barrel for manual actuation. A body of radiation-shielding material substantially covers the barrel, the body having a slot therein. A radiation-shielding unit is removably mounted over the slot. An aliquot of radioisotope-containing fluid is contained within the barrel. In the preferred embodiment of the invention, an optically-transparent radiation-shielding member is adapted for removable insertion over the slot. Before use of the syringe, the radiation-shielding unit, which provides protective shielding over the slot during shipping and storage, is removed and replaced by the optically transparent radiation-shielding member through which the user can view the syringe contents. In this embodiment the radiation-shielding unit comprises a shielding cover proportioned to cover the slot and a front flange extending downwardly from the front of the cover for providing shielding forwardly of the syringe body. The preferred embodiment further includes manually disengageable means for preventing a forward stroke of the plunger, preferably a clip engageable with the plunger.

25 Claims, 5 Drawing Figures

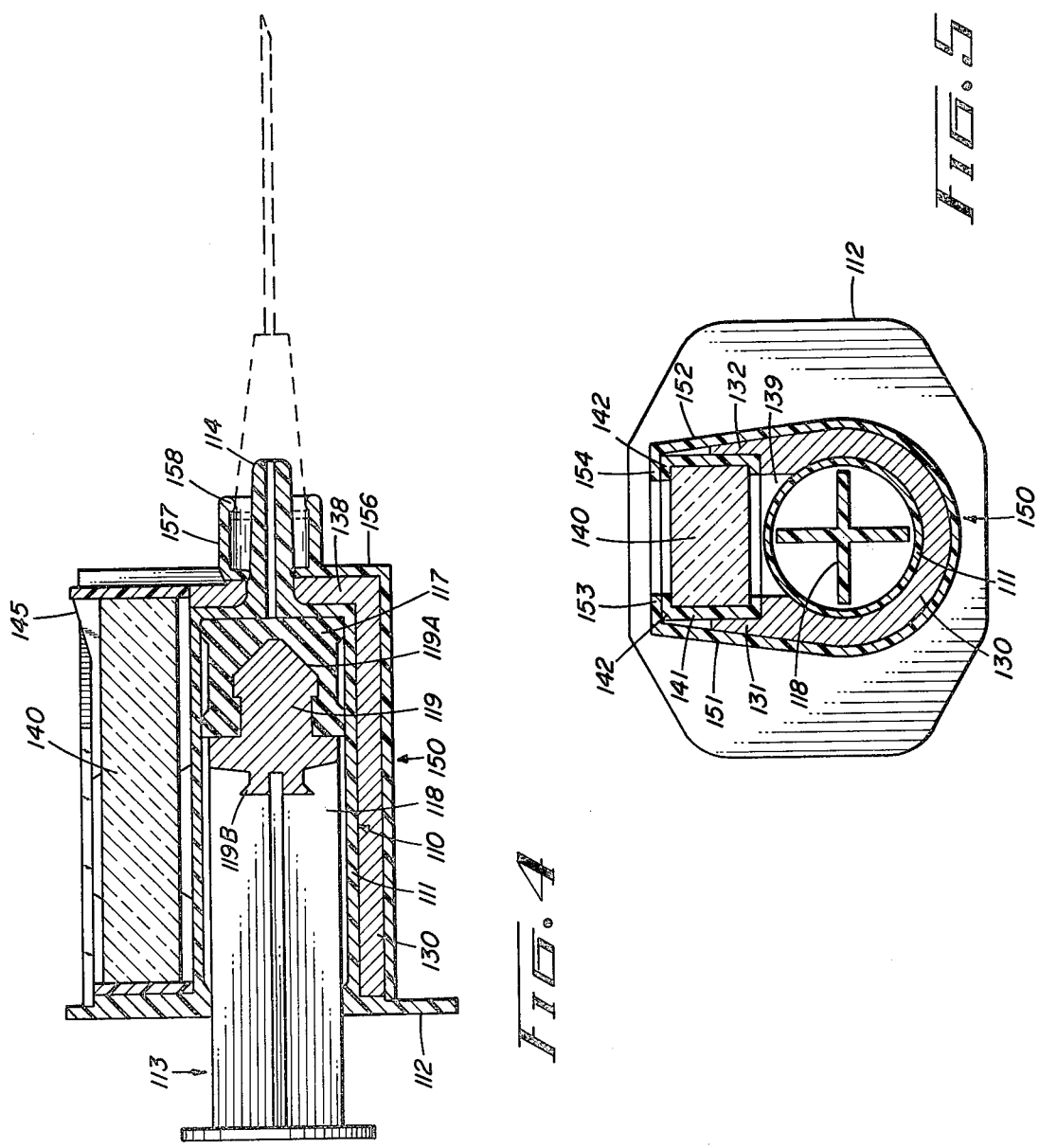

SYSTEM FOR TRANSPORTING, STORING AND INJECTING RADIOISOTOPE-CONTAINING FLUIDS

This is a continuation of application Ser. No. 747,557, filed Dec. 6, 1976, now abandoned.

BACKGROUND OF THE INVENTION

This invention relates to the storing, handling, and injecting of radioactive materials and, more particularly, to an improved system for storing, handling, and injecting radioactive isotope-containing fluids.

For various types of diagnostic testing it is necessary to inject radioactive materials into a patient. It is well recognized that technicians who handle these materials need protection against the perils of cumulative ionizing radiation exposure, so provision is commonly made for shielding the materials until such time as they are injected into the patient. Toward this end, various types of syringe shields have been developed. The typical prior art syringe shield includes a lead cylinder which fits over a syringe, the lead body having a window of leaded glass which allows the operator to see the scale on the syringe which is placed within the lead cylinder.

There are a number of disadvantages associated with commercially available syringe shield designs. Some units have a simple cylindrical casing which does not provide adequate shielding forwardly or rearwardly of the syringe length. A further problem is that there is no standardization of syringe sizes, and even syringes having the same volume often have different physical dimensions. For example, a 10 cc syringe may have various possible diameters depending on the particular manufacturer. Thus, special provision is generally necessary to fit a syringe shield to the different possible syringe sizes. For example, in one prior art design the syringe shield is provided with a "set screw" which adjustably protrudes into the syringe shield's bore and engages the syringe so that it cannot move around within the syringe shield. The use of this technique involves some inconvenience and can occasionally cause breakage of the syringe.

In addition to the difficulties encountered in the prior art due to the necessity for providing shielding for syringes which are used to inject materials emitting ionizing radiation, there are a number of distinct problems associated with the overall handling and storage of the radioactive materials. The procedure followed by a clinical facility utilizing injectable radioactive materials is generally as follows: a specified gross amount of material is ordered from a supplier in heavy shielded containers, these containers sometimes being in the form of a "generator" in which specified isotopes are converted to the form in which they are to be ultimately injected into a patient. Since the gross supply of material continuously loses potency, it has a limited life and material not utilized within a prescribed time loses its value. Accordingly, and since supplies are generally provided in relatively large containers, it is important to have a good estimate of the intended material requirements before ordering the supply for a given time period. However, since the number of patients to be tested during a given period is the subject of fortuitous circumstance, improper estimation and waste often result. When a patient is to be injected with a radioactive isotope, a technician will typically insert a syringe into a syringe shield and then transfer material from the supply case into the shielded syringe. Although shielding is utilized, this loading operation involves a risk of exposure. A further risk of exposure is involved if the technician requires an assay of the radioactive material now in the syringe, since the shielding is typically removed to perform this operation. Next, the radioactive material is injected into the patient, and the syringe shield is removed (and saved for the next usage) while the syringe is either disposed of or cleaned for subsequent usage. These operations involve some risk of residual contamination remaining on the shield or reusable syringe. Also, the overall above-described procedure involves substantial inconvenience of transferring materials, applying and removing shielding, and cleaning.

In the abovereferenced copending application Ser. No. 668,531, now U.S. Pat. No. 4,056,096, there is disclosed a shielded syringe suitable for partial disposability. It is an object of the present invention to further overcome the problems of the prior art as set forth and to provide a convenient system for transporting, storing and injecting radioactive isotope-containing fluids which minimizes risks of exposure, allows economies of ordering, is convenient to use, and is relatively inexpensive.

SUMMARY OF THE INVENTION

The present invention is directed to a system for transporting, storing, and injecting of radioactive isotopes, the system including a unit dose of radioactive isotope-containing fluid loaded in a disposable shielded syringe.

In accordance with the invention, there is provided a syringe body including a barrel and a plunger slideable in the barrel and extending from the rear of the barrel for manual actuation. A body of radiation-shielding material substantially covers the barrel, the body having a slot therein. A radiation-shielding unit is removably mounted over the slot. An aliquot of radioisotope-containing fluid is contained within the barrel.

In the preferred embodiment of the invention, an optically-transparent radiation-shielding member is adapted for removable insertion over the slot. Before use of the syringe, the radiation-shielding unit, which provides protective shielding over the slot during shipping and storage, is removed and replaced by the optically transparent radiation-shielding member through which the user can view the syringe contents. In this embodiment the radiation-shielding unit comprises a shielding cover proportioned to cover the slot and a front flange extending downwardly from the front of the cover for providing shielding forwardly of the syringe body. The preferred embodiment further includes manually disengageable means for preventing a forward stroke of the plunger, preferably a clip engageable with the plunger. Finally, in this embodiment, the plunger has a tip with the barrel, a stem coupled to the tip, and a plug of radiation-shielding material mounted rearwardly of the plunger tip, the plug conforming generally in shape to the inner surface of the barrel. The plug serves to shield an operator against radiation emitted axially from the rear of the barrel.

Further features and advantages of the invention will become more readily apparent from the following detailed description when taken in conjunction with the accompanying drawings.

BRIEF DESCRIPTION OF THE DRAWINGS

FIG. 4 is a cross-sectional view as taken through a section defined by arrows 4—4 of FIG. 3.

FIG. 5 is a cross-sectional view as taken through a section defined by arrows 5—5 of FIG. 3.

DESCRIPTION OF THE PREFERRED EMBODIMENT

Figure 1:
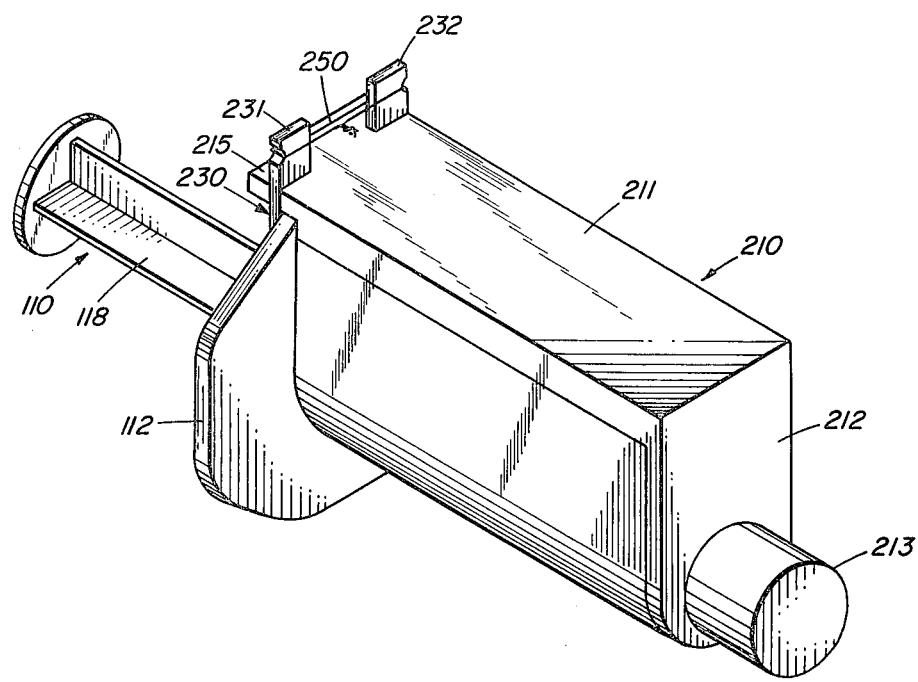
FIG. 1 is an elevational perspective view of an assembled system in accordance with an embodiment of the invention.
Figure 3:
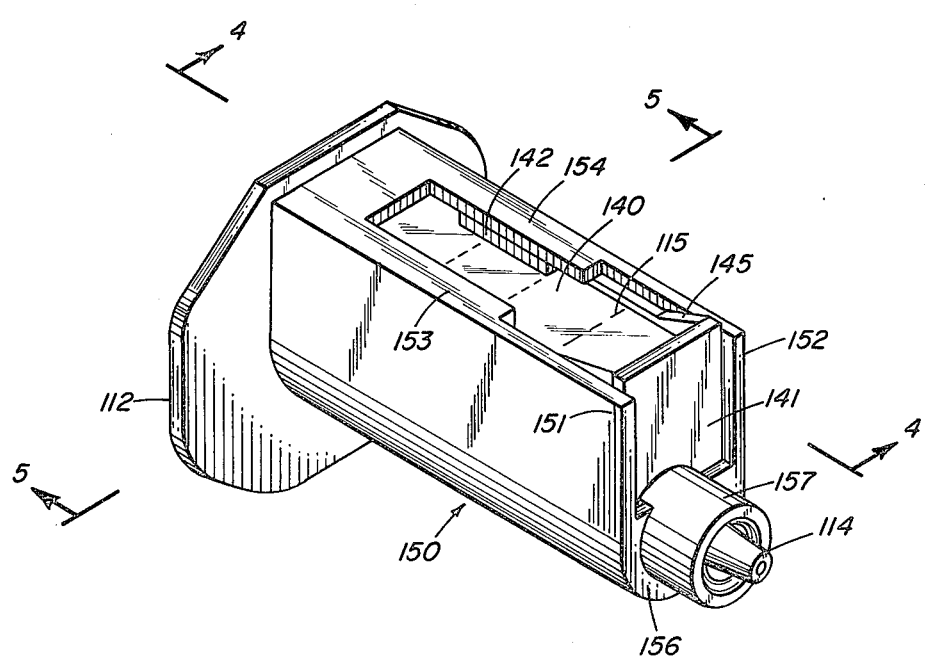
FIG. 3 is an elevational perspective view of a shielded syringe utilized in the system of FIG. 1.
Figure 2:
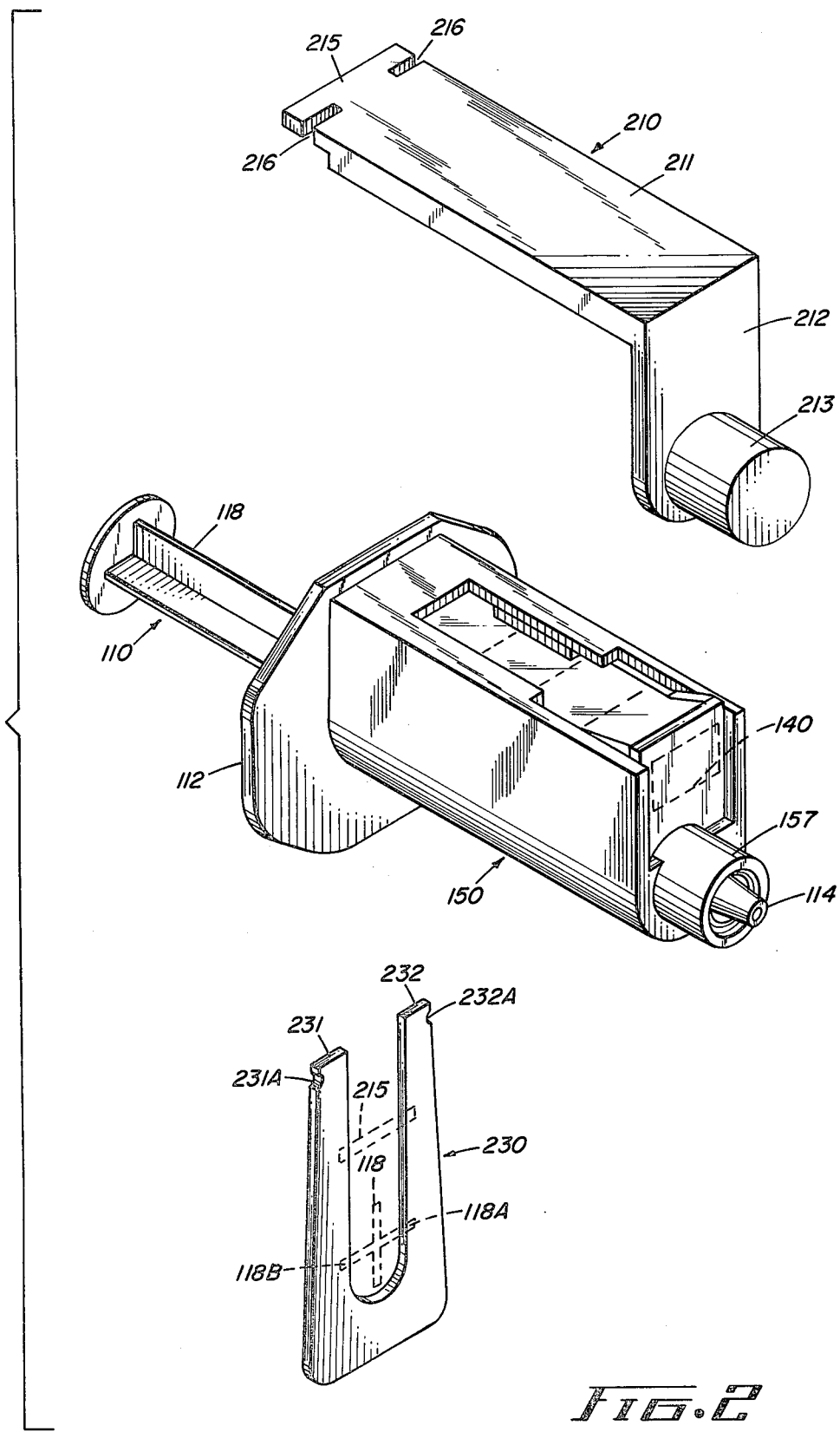
FIG. 2 is an exploded view of the system of FIG. 1.

FIGS. 1 and 2 illustrate the system of an embodiment of the invention with FIG. 1 showing the system in assembled form and ready for packaging or storage. To facilitate understanding of the invention, reference is first made to FIGS. 3-5 which illustrate the shielded syringe portion of the invention. The core of the shielded syringe includes the basic elements of a conventional disposable-type plastic syringe, as labeled in the drawings by reference numeral 110. The syringe 110 has a plastic body or barrel 111, a rear flange 112, a plunger 113 and a tip 114.

The plunger 113 has a conventional head or tip 117, typically formed of rubber, which is coupled to a plunger stem 118 by a novel shielding plug 119. The plug 119 is formed of a high density radiation-shielding material, such as lead or tantalum or plated lead. The plug has a cylindrical central portion which conforms generally to the inner circumference of the barrel 111, a front retaining nub 119A which is inserted in an aperture in the rear of tip 117, and a rear retaining nub 119B which snaps into and seats in the front end of the plunger stem 118. The plug 119 serves to shield the operator using the device against radiation emitted axially from the rear of the barrel. This radiation, which would typically and dangerously be directed toward the body of the operator, is generally not satisfactorily shielded in the prior art.

The syringe body has volumetric indicia disposed in a longitudinal pattern along its barrel as shown at 115. A generally cylindrical body 130 is formed of a radiation-shielding material, such as lead, and is proportioned such that its inner surface conforms generally to the outer surface of the syringe barrel 111. The body 130 tapers inwardly at its front end at 138 and has an elongated rectangular slot 139 extending along one side thereof, the slot being in registration with the indicia 15 on the barrel 111. The surface containing the slot is flat on top and a pair of panels 131 and 132, which can be formed integrally of the same radiation-shielding material such as lead, are spaced slightly from the parallel edges of the slot and extend outwardly from the flat surface.

A transparent radiation-shielding member 140 is of elongated rectangular shape and may be formed of leaded glass typically having a thickness which is substantially greater than that of the body 130. The member 140 is encased in a rectangular casing 141 which is opened at the top and bottom thereof. Pairs of lips 142 and 143 retain the member 140 within the casing 141. The top edge of the casing slants upward at the front thereof as shown at 145 so that the front end protrudes slightly above the top of the encased member 140. In the present embodiment the casing 141 is formed of material such as rigid plastic and the member 140 is snapped into the casing 141 for permanent retention therein and reuse in a manner to be described. The casing is proportioned to slideably fit within the panels 131 and 132 of body 130 such that the transparent shielding member 140 overlays the periphery of the slot 139 in body 130. As will be described, the encased member 140 is typically inserted in the shielded syringe at the time when it is to be used to inject a patient.

A shell 150 is preferably formed of rigid plastic and is proportioned to generally conform in shape to the outer surface of the body 130. Specifically, the shell 150 has a pair of side panels 151 and 152 which cover and extend above the body panels 131 and 132, respectively. The panels 151 and 152 have lips 153 and 154, respectively, which define an elongated slot that is in registration with the slot 139 in body 130. The front end of the shell 150 is about half opened and has an approximately semi-circular wall 156 having a circular aperture therein which receives the tip 114 of the syringe 110. The tip 114 is provided with an annular groove which is retained in the aperture as seen in FIG. 4. A cylindrical shroud 157 extends axially from the wall 156 and protrudes slightly above the top edge of the wall. The shroud 157, which may typically be formed integrally with the body, has an annular protrusion at 158.

To assemble the disposable portion of the device described thus far, the syringe 110, with its plunger in place, is inserted into the body 130. The syringe flange 112 has a wall member 112A formed on the inner surface thereof which serves as a spacer between the rear end of the body 130 and the flange. The syringe and body are then inserted into the open-ended rear of the shell. The rear edge of the shell fits over the periphery of wall 119 and is secured to the flange 112 by any suitable means, such as an epoxy bond. This assembly comprises the portion of the shielded syringe which is most suitable for disposability. FIG. 4 also shows the manner in which a standard needle can be mounted over the syringe tip and is conveniently retained within the shroud 157 by the annular protrusion 158. This eliminates the need for screwing in the needle and facilitates more convenient operation. However, it will be understood that a standard needle mounting, such as a Luer-lock mounting, can be employed.

In accordance with the invention, an aliquot of radioisotope-containing fluid is loaded into the syringe barrel before packaging. In the embodiment of FIGS. 1 and 2, a multipurpose sub-assembly is provided to deal with the presence of the radioisotope fluid. A radiation-shielding unit 210 includes a cover 210 which is proportioned at least large enough to cover the slot 139 (FIG. 5). In the present embodiment, a flange 212 extends downwardly from the front edge of the cover 211 and is formed integrally therewith. A hollow shroud 213, having a closed front end, protrudes from the flange at a position thereon which is in registration with the position of the tip 114 of the syringe. The rear end of the cover 211 has a reduced thickness, as shown, to fit over the flange 112. A protruding rear handle 215 has an indented neck portion 216 which extends from the rear edge of the cover 211. In the present embodiment, the shielding unit 210, including the cover 211, the front flange 212, the shroud 213 and the necked handle 215 are integrally formed of a single piece of radiation-shielding material, such as lead. The lead may be plastic coated or plated, if desired.

The embodiment of FIGS. 1 and 2 further includes a horseshoe-shaped clip 230 which may be formed of any suitable material, but is preferably formed of plastic. The plunger stem 118 has a pair of slots in opposite sides of one of its cross panels, as depicted in dotted line in FIG. 2 (the stem itself being shown in dashed line). The slots are referred to by reference numerals 118A and 118B. The clip 230 is proportioned to engage the slots 118A and 118B when the plunger 110 is in its fully extended position. The spaced ends 231 and 232 of the clip are proportioned to engage the neck 216 of the rear handle of shielding unit 210 when the unit is positioned in place over the slot 139 (see dashed line depiction in FIG. 2).

Operation of the invention is as follows: at the packaging facility, the aliquot of radioisotope is indroduced into the barrel 111 of syringe 110. The shielding unit 210 is positioned over the slot in the syringe shielding body with the shroud 213 covering the protruding tip of the syringe. The clip 230 is then engaged with the slots in the plunger stem, the ends of the clip engaging the neck portion of the rear handle 215 of unit 210. Depressions 231A and 232A are provided in the clip, and a retaining wire is wrapped around the depressed regions. The clip is formed of a material, such as plastic, which is sufficiently flexible to yield slightly to engage the plunger and cover unit. The overall system is typically stored in a carton for transporting. It is seen that the clip serves to retain the plunger in the fully extended position to prevent accidental depression thereof during shipping. The clip also retains the shielding unit 210 in place. The shielding unit, in conjunction with the disposable shielded syringe, is seen to render the radioisotope material completely shielded, the cover 211 providing shielding above the aperture, and the front flange and shroud providing shielding forwardly of the syringe body. The shielding plug 119 (FIG. 4) provides shielding in the rear axial direction.

When the assembly is to be used, it is removed from its carton and the wire 250 and clip 230 are removed. This serves to release the plunger 110 for subsequent activation and also to release the shielding unit 210 which can now be removed. If desired, the reusable optically-transparent radiation-shielding member 140 (FIGS. 3-5, and in dashed line in FIG. 2) can now be inserted over the slot 139 to provide shielding during usage while still allowing the operator to view the contents of the shielded syringe. In the present embodiment, the encased transparent shielding member 140 is inserted in the shell through the front opening therein and is retained from sliding out during use by the protruding portion of the shroud 157. If desired, an assay can be performed prior to insertion of the leaded glass shielding member.

After injection of the unit dose of radioisotope into the patient, the leaded glass shielding member 140 is removed for use in conjunction with other disposable systems, and the remainder of the system can be discarded (removal being facilitated by the raised edge of the casing (145) which can be grasped such as by using the thumb and finger). Thus, virtually complete shielding is provided from the time of packaging until use, handling of radioisotope materials is eliminated, and the inconvenience of handling shielding media and of measuring are all eliminated. The portion of the system which is disposable is relatively inexpensive to manufacture and the relatively expensive leaded-glass is reusable. In addition to the advantages in safety and convenience, the need to clean contaminated shields is eliminated.

The invention has been described with reference to a particular embodiment, but variations within the spirit and scope of the invention will occur to those skilled in the art. For example, it will be recognized that the shielding unit 210 could be in the form of a lead slug (having the shape of the member 140—see the dashed outline of FIG. 2) in those situations where the full front shielding is considered unnecessary.

We claim:

1. A system for transporting, storing and injecting radioactive material, comprising:
    a syringe body including a barrel and a plunger slideable in said barrel, said plunger extending from the rear of said barrel for manual actuation;
    a body of radiation-shielding material substantially covering said barrel, said body having a slot therein;
    a radiation-shielding unit removably mounted over said slot;
    an aliquot of radioisotope-containing fluid contained in said barrel; and
    manually disengageable means for preventing a forward stroke of said plunger.

2. The system as defined by claim 1 further comprising an optically-transparent radiation-shielding member adapted for removable insertion over said slot.

3. The system as defined by claim 2 wherein said radiation-shielding unit comprises a radiation-shielding cover which covers said slot and a front flange extending downwardly from the front of said cover for providing shielding forwardly of said syringe body.

4. The system as defined by claim 3 wherein said manually disengageable means for preventing a forward stroke of said plunger comprises a clip engageable with said plunger.

5. The system as defined by claim 4 wherein said cover unit further comprises a rear handle engageable with said clip, whereby said clip prevents motion of said plunger and also retains said cover unit in position.

6. The system as defined by claim 1 wherein said plunger has a tip within said barrel, a stem coupled to said plunger tip and a plug of radiation-shielding material mounted rearwardly of said plunger tip, said plug conforming generally in shape to the inner surface of said barrel.

7. The system as defined by claim 1 wherein said radiation-shielding unit comprises a radiation-shielding cover which covers said slot and a front flange extending downwardly from the front of said cover for providing shielding forwardly of said syringe body.

8. The system as defined by claim 7 wherein said syringe body includes a syringe tip extending forwardly of said body of radiation-shielding material and wherein said cover unit further comprises a hollow shroud mounted on said flange and proportioned to cover said extending tip.

9. The system as defined by claim 1 wherein said manually disengageable means for preventing a forward stroke of said plunger comprises a clip engageable with said plunger.

10. A system for transporting, storing and injecting an aliquot of radioisotope-containing fluid, comprising:
    a syringe having a barrel and a plunger slideable in the barrel, said plunger extending from the rear of said barrel for manual actuation;

a body of radiation-shielding material substantially covering the barrel of said syringe, said body having a slot therein;

a radiation-shielding unit removably mounted over said slot; and manually disengageable means for preventing a forward stroke of the plunger.

11. The system as defined by claim 10 further comprising an optically-transparent radiation-shielding member adapted for removable insertion over said slot.

12. The system as defined by claim 11 wherein said radiation-shielding member is formed of leaded glass.

13. The system as defined by claim 10 wherein said plunger has a tip within said barrel, a stem coupled to said plunger tip and a plug of radiation-shielding material mounted rearwardly of said plunger tip, said plug conforming generally in shape to the inner surface of said barrel.

14. The system as defined by claim 10 wherein said radiation-shielding unit comprises a radiation-shielding cover which covers said slot and a front flange extending downwardly from the front of said cover for providing shielding forwardly of said syringe body.

15. The system as defined by claim 14 wherein said syringe includes a syringe tip extending forwardly of said body of radiation-shielding material and wherein said cover further comprises a hollow shroud mounted on said flange and proportioned to cover said extending tip.

16. The system as defined by claim 10 wherein said manually disengageable means for preventing a forward stroke of said plunger comprises a clip engageable with said plunger.

17. A system for transporting, storing and injecting radioactive material, comprising:

a syringe body including a barrel and a plunger slideable in said barrel, said plunger extending from the rear of said barrel for manual actuation;

a body of radiation-shielding material substantially covering said barrel, said body having a slot therein;

a radiation-shielding unit removably mounted over said slot, said radiation-shielding unit comprising a radiation-shielding cover which covers said slot and a front flange extending downwardly from the front of said cover for providing shielding forwardly of said syringe body; and an aliquot of radioisotope-containing fluid contained in said barrel.

18. The system as defined by claim 17 wherein said syringe body includes a syringe tip extending forwardly of said body of radiation-shielding material and wherein said cover unit further comprises a hollow shroud mounted on said flange and proportioned to cover said extending tip.

19. A system for transporting, storing and injecting an aliquot of radioisotope-containing fluid, comprising:

a syringe having a barrel and a plunger slideable in the barrel, said plunger extending from the rear of said barrel for manual actuation;

a body of radiation-shielding material substantially covering the barrel of said syringe, said body having a slot therein; and a radiation-shielding unit removably mounted over said slot; said radiation-shielding unit comprising a radiation-shielding cover which covers said slot and a front flange extending downwardly from the front of said cover for providing shielding forwardly of said syringe body.

20. The system as defined by claim 19 further comprising an optically-transparent radiation-shielding member adapted for removable insertion over said slot.

21. The system as defined by claim 19 wherein said syringe includes a syringe tip extending forwardly of said body of radiation-shielding material and wherein said cover further comprises a hollow shroud mounted on said flange and proportioned to cover said extending tip.

22. A method for loading, transporting, storing, and injecting radioactive material for diagnostic testing, comprising the steps of:

pre-loading, at one location, an aliquot of radioisotope-containing fluid in a shielded syringe having a slot in the shielding thereof and a shielding unit removably mounted over the slot;

transporting said preloaded shielded syringe to another location;

removing the shielding unit and inserting an optically transparent radiation-shielding member over the slot to allow safe viewing of the contents of said syringe; and injecting the fluid in said syringe into a patient.

23. The method as defined by claim 22 further comprising the steps of locking the syringe plunger after the preloading step; and unlocking the syringe plunger before the injecting step.

24. The method as defined by claim 23 further comprising the steps of removing the optically transparent radiation-shielding member after the injecting step, and disposing of the spent shielded syringe.

25. The method as defined by claim 24 further comprising the steps of removing the optically transparent radiation-shielding member after the injecting step, and disposing of the spent shielded syringe.

* * * * *